United States Patent [19]

Hiiro et al.

[11] 4,115,426

[45] Sep. 19, 1978

[54] METHOD FOR THE PREPARATION OF DIALKYLCHLOROSILANES

[75] Inventors: Takeshi Hiiro; Hideki Sakurai, both of Sendai; Fumihiko Kondo, Kawagoe, all of Japan

[73] Assignees: Kawaken Fine Chemicals Co., Ltd.; Shin-Etsu Chemical Co., Ltd., both of Tokyo, Japan

[21] Appl. No.: 871,848

[22] Filed: Jan. 24, 1978

[30] Foreign Application Priority Data

Feb. 2, 1977 [JP] Japan .................................. 52/10373

[51] Int. Cl.$^2$ .............................................. C07F 7/12
[52] U.S. Cl. ............................................. 260/448.2 E
[58] Field of Search ................................. 260/448.2 E

[56] References Cited

PUBLICATIONS

Noll, "Chemistry and Technology of Silicones", Academic Press, N. Y. (1968), pp. 87–88.

Primary Examiner—Paul F. Shaver
Attorney, Agent, or Firm—Toren, McGeady and Stanger

[57] ABSTRACT

A novel and effective method for the synthetic preparation of dialkylchlorosilanes as an important intermediate in the silicone industry is provided, which is based on the selectivity of a specific combination of a reaction solvent and a reducing agent in the dechlorination-reduction of one of the two silicon-bonded chlorine atoms present in a dialkyldichlorosilane to convert the Si-Cl linkages to Si-H. The reaction solvent used is either N,N'-dimethylimidazolidinone or N,N,N',N',N",N"-hexamethyl-phosphoric triamide, while the reducing agent is sodium borohydride, optionally in combination with sodium hydride.

8 Claims, No Drawings

METHOD FOR THE PREPARATION OF DIALKYLCHLOROSILANES

BACKGROUND OF THE INVENTION

The present invention relates to a novel method for the preparation of a diorganochlorosilane or, in particular, a dialkylchlorosilane by the selective reduction of a dialkyldichlorosilane whereby only one of the two chlorine atoms present in the dialkyldichlorosilane is reduced and replaced with a hydrogen atom.

Dialkylchlorosilanes represented by the general formula $R_2SiClH$, where R is an alkyl group, are important monomeric starting materials in the silicone industry, widely employed, for example, in the manufacture of silicone fluids having silicon-bonded hydrogen atoms Si—H as functional groups in the main chain or at the terminals of the siloxane chains. The dialkylchlorosilanes are also useful as an intermediate compound in the synthetic preparation of various kinds of organosilicon compounds. Therefore, it has eagerly been desired to establish a method for economical preparation of such dialkylchlorosilanes.

Despite a large commercial demand for dialkylchlorosilanes, no economical manufacturing methods have been established. For example, dimethylchlorosilane has been supplied only as a by-product obtained in the synthesis of dimethyldichlorosilane. That is to say, dimethylchlorosilane is contained in a low boiling fraction from the synthesis of dimethyldichlorosilane and isolated by distillating the fraction.

A possible synthetic procedure for a dialkylchlorosilane may be the selective reduction of one of the two chlorine atoms in the corresponding dialkyldichlorosilane to convert the Si—Cl linkages to Si—H, using a suitable reducing agent, such as lithium aluminum hydride, which is known to be effective for reducing the Si—Cl to Si—H. Lithium aluminum hydride has, however, no satisfactory selectivity in the reduction of dialkyldichlorosilane producing dialkylsilane, $R_2SiH_2$, by the dechlorination reduction of both of the two chlorine atoms in the starting silane. Thus no reducing agent having a sufficient selectivity has been available for the direct reduction of dialkyldichlorosilanes to the desired dialkylchlorosilanes.

Several alternative methods have been reported in literature for the preparation of dimethylchlorosilane. For example, a polydimethylsilane having —(CH$_3$)$_2$Si— units as the recurring units is subjected to a cleavage reaction by passing hydrogen chloride gas under irradiation with ultraviolet light (see Chemical Communications, 1970, p. 507) to produce dimethylchlorosilane. As another example, dimethyldichlorosilane is reacted with diethylamine to produce dimethyl(N,N-diethylamino)chlorosilane which is reduced with lithium aluminum hydride to dimethylchlorosilane (see Journal of Organometallic Chemistry, 18 (1969), P. 371). As a further example, dimethyldichlorosilane is reduced with sodium hydride in the presence of aluminum chloride to dimethylchlorosilane (see Zhurnal Obshchei Khimii, 40 (1970), p. 812). These synthetic methods, however, are disadvantaged by the complexity of the reaction procedures that require special skills to achieve satisfactory results.

SUMMARY OF THE INVENTION

The object of the present invention is, therefore, to provide a novel and effective method for the preparation of a dialkylchlorosilane by the selective reduction of the corresponding dialkyldichlorosilane whereby only one of the silicon-bonded chlorine atoms present in the starting silane is converted to a silicon-bonded hydrogen atom.

The invention has been completed as a result of extensive investigations by the inventors to discover a specifically effective combination of a reducing agent and a solvent to be used in the reaction. In the method of the present invention, a dialkyldichlorosilane is reduced with sodium borohydride, optionally combined with sodium hydride, as the reducing agent in a solvent which is either N,N'-dimethylimidazolidinone or N,N,N', N', N'', N''-hexamethylphosphoric triamido.

DETAILED DESCRIPTION OF THE PREFERRED EMBODIMENTS

The dialkyldichlorosilanes as the starting material in the method of the present invention are represented by the general formula $$R_2SiCl_2$$

where R is an alkyl group having, in particular, from 1 to 4 carbon atoms, such as methyl, ethyl, propyl and butyl groups. Illustrative of the dialkyldichlorosilanes are dimethyldichlorosilane, diethyldichlorosilane, di(isopropyl)dichlorosilane, and di(n-butyl)-dichlorosilane. These silanes can be reduced by the method of the invention to corresponding dialkylchlorosilane, such as dimethylchlorosilane, diethylchlorosilane, di(isopropyl)chlorosilane, and di(n-butyl)-chlorosilane, respectively.

The reducing agents useful in the method of the invention, i.e. sodium borohydride and sodium hydride, are soluble in N,N'-dimethylimidazolidinone (which is hereinafter briefly mentioned as DMI) and N,N,N',N', N'', N''-hexamethylphosphoric triamide (which is hereinafter briefly mentioned as HMPA).

The reaction according to the present invention is conveniently performed by adding the dialkyldichlorosilane to the solution of the reducing agent in the solvent and heating the mixture at an elevated temperature of, say 30° to 100° C. or, preferably, from 40° to 80° C. under agitation. After completion of the reaction taking from 2 to 3 hours depending on the conditions, the product dialkylchlorosilane is isolated by distillating the reaction mixture and the solvent is recovered by further distillation of a residual high boiling fraction.

The reducing agent essential in the method of the present invention is sodium borohydride, NaBH$_4$, and used in an amount of from 0.3 to 1.5 moles per mole of the starting dialkyldichlorosilane. It is natural that any smaller amounts result in an insufficient yield of the desired dialkylchlorosilane, while any larger amounts are disadvantageous due to the increased formation of the dialkylsilane as the by-product by further reduction of the silicon-bonded chlorine atoms.

The use of sodium borohydride, which is rather an expensive reducing agent, can be saved by combination with sodium hydride. In the case of such combination, the total amount of the two reducing agents is preferably in the range from 0.5 to 1.5 moles per mole of the starting silane. It is recommended that at least one-fourth in mole of the combination is sodium borohydride. If the proportion of sodium borohydride in the combination is smaller, the reaction velocity concerned is very much reduced, leading to a lower yield or productivity of the desired silane product.

The specificity of the combination of the solvent and the reducing agent is very remarkable for the dechlorination reduction of the silicon-bonded chlorine atoms. This may be demonstrated by the fact that no desired reaction takes place at all when a conventional solvent, such as diethyl ether, tetrahydrofuran, benzene, toluene and the like, is used or when no solvent is used, despite the use of sodium borohydride as the reducing agent. Sodium hydride is too active to be selective, especially, at elevated temperatures in the reduction of dialkyldichlorosilanes, where both of the two silicon-bonded chlorine atoms in the dialkyldichlorosilane are reduced to form the dialkylsilane, while no reaction takes place at room temperature or below.

The amount of DMI or HMPA used as the solvent in the method of the present invention is from 80 to 700 parts by weight or, preferably, from 100 to 500 parts by weight per 100 parts by weight of the dialkyldichlorosilane as the starting material. The reaction velocity is decreased with smaller amounts of the solvent, accompanied by eventual predominance of undesirable side reactions, such as the formation of dialkylsilane which works to decrease the yield of the desired dialkylchlorosilane. Without the solvent, no reaction proceeds. On the other hand, larger amounts of the solvent do not bring about any particular, additional advantages and should not be recommendable from an economical point of view.

The mechanism of the advantageous selectivity in reduction obtained by the specific combination of the reducing agent and the solvent in accordance with this invention is not well understood but presumably as follows. When the reaction is carried out without the solvent or in a non-polar solvent, such as diethyl ether, tetrahydrofuran, benzene, or toluene, the nucleophilic attack of the borohydride ions toward the silicon atoms is suppressed by strong ion pairs formed between the sodium ions and the borohydride ions of the sodium borohydride, resulting in an undesired reaction to the formation of the dialkylchlorosilane. On the contrary, the sodium ions of sodium borohydride are strongly solvated in a polar solvent, such as DMI or HMPA, resulting in turn in the activation of the borohydride counter ions to a level suitable for the selective reduction of the silicon-bonded chlorine atoms.

An additional advantage obtained by the use of DMI or HMPA as the solvent is that the solvent is stable and non-reactive with the starting silanes as well as with the product silanes. Another advantage is that the product silanes can be readily separated from the solvent by distillation owing to a large difference between the boiling point of the solvent and that of the product silane which is a lower alkyl derivative having a sufficiently lower boiling point than the solvent.

The following examples illustrate the method of the present invention in further detail.

EXAMPLE 1.

Into a flask equpped with a cooling tube which is connected to a cold trap in a Dry-Ice bath through a drying tube filled with calcium chloride, a thermometer, a dropping funnel and a stirrer, 100 ml of HMPA and 3.8 g of sodium borohydride were charged, the latter being dissolved in the former. Into the resulting solution 25.8 g of dimethyldichlorosilane was dropped under agitation through the dropping funnel over a period of 15 minutes. Thereupon, the reaction mixture was heated to a temperature of 50° C., at which the reaction was continued for about 2 hours. After completion of the reaction, the pressure inside the flask was reduced by use of an aspirator connected to the cold trap to distill out and collect low boiling matter in the trap which was cooled with a Dry-Ice bath. The distillate thus collected in the trap was subjected to distillation to produce 13.4 g of a fraction boiling at 34° to 35° C. This fraction was identified by the NMR analysis to be dimethylchlorosilane with a 71% yield of the theoretical.

The data of the NMR analysis obtained with carbon tetrachloride as the solvent were as follows:

$\delta = 0.45$ p.p.m. assigned to the hydrogen atoms in —Si(CH$_3$)$_3$ groups.

$\delta = 4.85$ p.p.m. assigned to the hydrogen atoms in —Si—H groups.

EXAMPLE 2.

The reaction was carried out in the same manner as in Example 1 using 50 ml of DMI and 5.7 g of sodium borohydride to form a solution, and 38.7 g of dimethyldichlorosilane which was dropped into the solution over a period of about 30 minutes. The yield of dimethylchlorosilane was 16.1 g corresponding to 57% of the theoretical.

Further, the same procedure as above was repeated except that the amount of DMI was 23 ml instead of 50 ml, the yield of dimethylchlorosilane was 1.5 g. This is understood to indicate the criticality of DMI as the solvent.

EXAMPLE 3.

The reaction was carried out in the same manner as in Example 1 using 50 ml of HMPA and 1.9 g of sodium borohydride to form a solution, and 15.7 g of diethyldichlorosilane which was dropped into the solution over a period of about 10 minutes. The desired diethylchlorosilane boiling at 96° to 98° C. was obtained at a yield of 5.0 g corresponding to 41% of the theoretical.

EXAMPLE 4.

The same experimental procedure as in Example 2 was undertaken except that the amount of sodium borohydride was decreased to 2.84 g instead of 5.7 g and 4.50 g of sodium hydride was added in combination with sodium borohydride. The yield of dimethylchlorosilane was 13.1 g corresponding to 46% of the theoretical.

EXAMPLE 5.

This is a comparative example.

Into a suspension of 15.1 g of sodium borohydride in 400 ml of xylene contained in the same apparatus as used in Example 1 was dropped 103.3 g of dimethyldichlorosilane over a period of about 15 minutes. The resulting mixture was heated at 50° to 60° C. for about 2 hours with agitation. After the end of the above reaction time, low boiling matter was distilled off from the reaction mixture under reduced pressure and collected in the cold trap cooled with a Dry-Ice bath. The analysis of this low boiling fraction indicated that the fraction was the starting dimethyldichlorosilane itself and did not contain dimethylchlorosilane as the desired reaction product.

What is claimed is:

1. A method for the preparation of a dialkylchlorosilane which comprises reducing a dialkyldichlorosilane with sodium borohydride in a solvent capable of dissolving sodium borohydride.

2. The method as claimed in claim 1 wherein the solvent is N,N'-dimethylimidazolidinone.

3. The method as claimed in claim 1 wherein the solvent is N,N,N',N',N'',N''-hexamethylphosphoric triamide.

4. The method as claimed in claim 1 wherein the reduction of the dialkyldichlorosilane with sodium borohydride is carried out at a temperature in the range from 30° to 100° C.

5. The method as claimed in claim 1 wherein the amount of sodium borohydride is in the range from 0.3 to 1.5 moles per mole of the dialkyldichlorosilane.

6. The method as claimed in claim 1 wherein the amount of the solvent is in the range from 80 to 700 parts by weight per 100 parts by weight of the dialkyldichlorosilane.

7. The method as claimed in claim 1 wherein sodium borohydride is partly replaced with sodium hydride.

8. The method as claimed in claim 7 wherein the proportion of sodium borohydride to sodium hydride is at least 1:3 by mole.

* * * * *